United States Patent
Kimura et al.

(10) Patent No.: US 10,329,218 B2
(45) Date of Patent: Jun. 25, 2019

(54) ISOMERIZATION CATALYST, METHOD FOR PRODUCING STRAIGHT-CHAIN OLEFIN, AND METHOD FOR PRODUCING COMPOUND

(71) Applicant: JXTG NIPPON OIL & ENERGY CORPORATION, Tokyo (JP)

(72) Inventors: Nobuhiro Kimura, Tokyo (JP); Sosuke Higuchi, Tokyo (JP); Junji Wakabayashi, Tokyo (JP); Atsushi Segawa, Tokyo (JP)

(73) Assignee: JXTG NIPPON OIL & ENERGY CORPORATION, Tokyo (JP)

( * ) Notice: Subject to any disclaimer, the term of this patent is extended or adjusted under 35 U.S.C. 154(b) by 10 days.

(21) Appl. No.: 15/575,484

(22) PCT Filed: May 27, 2016

(86) PCT No.: PCT/JP2016/065748
§ 371 (c)(1),
(2) Date: Nov. 20, 2017

(87) PCT Pub. No.: WO2016/194822
PCT Pub. Date: Dec. 8, 2016

(65) Prior Publication Data
US 2018/0170833 A1    Jun. 21, 2018

(30) Foreign Application Priority Data

May 29, 2015  (JP) .................................. 2015-110044

(51) Int. Cl.
| | | |
|---|---|---|
| *C07C 5/25* | (2006.01) |
| *B01J 21/12* | (2006.01) |
| *B01J 29/08* | (2006.01) |
| *B01J 29/40* | (2006.01) |
| *B01J 29/70* | (2006.01) |
| *B01J 29/85* | (2006.01) |
| *C07C 5/333* | (2006.01) |
| *C07C 45/50* | (2006.01) |

(52) U.S. Cl.
CPC ............. *C07C 5/2518* (2013.01); *B01J 21/12* (2013.01); *B01J 29/08* (2013.01); *B01J 29/40* (2013.01); *B01J 29/70* (2013.01); *B01J 29/85* (2013.01); *C07C 5/333* (2013.01); *C07C 45/50* (2013.01); *C07C 2521/12* (2013.01); *C07C 2529/06* (2013.01); *C07C 2529/08* (2013.01); *C07C 2529/40* (2013.01); *C07C 2529/70* (2013.01); *C07C 2529/85* (2013.01)

(58) Field of Classification Search
CPC ......... C07C 5/33; C07C 5/2518; C07C 45/50; C07C 2521/12
See application file for complete search history.

(56) References Cited

U.S. PATENT DOCUMENTS

| | | |
|---|---|---|
| 3,642,933 A | 2/1972 | Heckelsberg |
| 3,749,415 A | 7/1973 | Sampatacos |
| 4,229,610 A | 10/1980 | Myers et al. |
| 4,289,919 A | 9/1981 | Myers |
| 2007/0173677 A1* | 7/2007 | Fujikawa .............. C07B 37/08 585/670 |
| 2010/0048959 A1 | 2/2010 | Sigl et al. |

FOREIGN PATENT DOCUMENTS

| | | |
|---|---|---|
| CA | 1193238 A | 9/1985 |
| CA | 1199041 A | 1/1986 |
| DE | 3319099 A1 | 12/1983 |
| DE | 33191971 A1 | 12/1983 |
| JP | H08224470 A | 9/1996 |
| JP | H10167989 A | 6/1998 |
| JP | H10167992 A | 6/1998 |
| JP | 2004530716 A | 10/2004 |
| JP | 2005239651 A | 9/2005 |
| JP | 2008-525187 A | 7/2008 |
| JP | 2009-539747 A | 11/2009 |
| JP | 2010511015 A | 4/2010 |
| WO | 03000631 A1 | 1/2003 |
| WO | 2014112522 A1 | 7/2014 |

OTHER PUBLICATIONS

International Search Report from Application No. PCT/JP2016/065748 dated Aug. 9, 2016.
International Preliminary Report on Patentability from Application No. PCT/JP2016/065748 dated Dec. 5, 2017.
Written Opinion of the International Searching Authority from Application No. PCT/JP2016/065748 dated Aug. 9, 2016.
Office Action issued in counterpart Japanese Patent Application No. P2015-110044 dated Jul. 31, 2018.

* cited by examiner

*Primary Examiner* — Sikarl A Witherspoon
(74) *Attorney, Agent, or Firm* — Greenblum & Bernstein, P.L.C.

(57) ABSTRACT

An isomerization catalyst for isomerizing a first straight-chain olefin to a second straight-chain olefin different therefrom in a double bond position in the presence of 20 ppm by volume or more of molecular oxygen and/or water, comprising: Si; and Al.

15 Claims, No Drawings

ISOMERIZATION CATALYST, METHOD FOR PRODUCING STRAIGHT-CHAIN OLEFIN, AND METHOD FOR PRODUCING COMPOUND

TECHNICAL FIELD

The present invention relates to isomerization catalysts and methods for producing straight-chain olefins using the isomerization catalyst. The present invention also relates to methods for producing compounds derived from straight-chain olefins.

BACKGROUND ART

Straight-chain olefins each having one double bond in the molecule thereof are useful as basic chemical raw materials in the petrochemical industry, and the uses thereof differ depending on the positions of the double bonds in the molecules thereof. Internal olefins having a double bond internally are used as reaction raw materials of reactions such as hydrogenation and alkylation. Meanwhile, terminal olefins having a double bond terminally are used for reactions such as dehydrogenation, hydroformylation and oligomerization. Terminal olefins of C4 to C8 used with ethylene as comonomers among terminal olefins when linear low density polyethylene (LLDPE) is produced (for example, 1-butene, 1-hexene, and 1-octane) is economically important, in particular. Additionally, 1-butene is used also for producing butadiene, 1-polybutene, and buteneoxide.

Straight-chain olefins having a double bond terminally (for example, 1-butene) can be produced, for example, by isomerizing straight-chain olefins having a double bond internally and corresponding thereto (for example, 2-butene) by catalysts.

For example, catalytic reactions in which straight-chain olefins having an internal double bond are isomerized to straight-chain olefins having a terminal double bond are disclosed in Patent Literature 1 to 5.

CITATION LIST

Patent Literature

Patent Literature 1: U.S. Pat. No. 3,642,933
Patent Literature 2: U.S. Pat. No. 4,229,610
Patent Literature 3: German Patent No. 3319171
Patent Literature 4: German Patent No. 3319099
Patent Literature 5: U.S. Pat. No. 4,289,919

SUMMARY OF INVENTION

Technical Problem

However, methods for the position isomerization of olefins by using conventional isomerization catalysts were difficult to use industrially since there are drawbacks such as decreases in product purity due to the proceeding of side reactions, insufficient yields, and marked deterioration of catalysts under conditions where oxygen or water exists substantially.

One of the objects of the present invention is to provide an isomerization catalyst enabling the efficient isomerization reaction of an olefin with catalyst deterioration suppressed enough under even conditions where oxygen or water exists substantially. One of the objects of the present invention is to provide a method for producing a straight-chain olefin by using the above isomerization catalyst. One of the objects of the present invention is to provide a method for producing a compound derived from the isomerized straight-chain olefin by reacting the straight-chain olefin to obtain the compound.

Solution to Problem

An isomerization catalyst according to an aspect of the present invention is a catalyst for isomerizing a first straight-chain olefin to a second straight-chain olefin different therefrom in a double bond position in the presence of 20 ppm by volume or more of molecular oxygen and/or water, wherein the catalyst comprises Si and Al.

The amount $A_1$ of the total acid sites on an isomerization catalyst according to an aspect of the present invention measured by ammonia temperature programmed desorption may be 0.11 mmol/g or less.

The ratio $A_2/A_1$ of the amount $A_2$ of acid sites measured in the temperature range of 600° C. or more to the amount $A_1$ of the total acid sites on an isomerization catalyst according to an aspect of the present invention as measured by ammonia temperature programmed desorption may be 0.03 or more.

An isomerization catalyst according to an aspect of the present invention may be a catalyst containing a zeolite.

As to an isomerization catalyst according to an aspect of the present invention, the molar ratio of Si to Al (Si/Al) may be 100 or more.

A method for producing a straight-chain olefin according to an aspect of the present invention comprises: a step of contacting a raw material compound containing a first straight-chain olefin with the above isomerization catalyst in the presence of 20 ppm by volume or more of molecular oxygen and/or water to isomerize at least a portion of the above first straight-chain olefin to a second straight-chain olefin different therefrom in double bond position.

In a method for producing a straight-chain olefin according to an aspect of the present invention, the number of carbon atoms of the above first and second straight-chain olefins may be 4 to 8.

In a method for producing a straight-chain olefin according to an aspect of the present invention, the above step may be performed under conditions for a gas-solid catalytic reaction.

A method for producing a compound according to an aspect of the present invention may comprise: a first step of contacting a first raw material compound containing a first straight-chain olefin with the above isomerization catalyst in the presence of 20 ppm by volume or more of molecular oxygen and/or water to isomerize at least a portion of the above first straight-chain olefin to a second straight-chain olefin different therefrom in a double bond position; and a second step of reacting a second raw material compound containing the above second straight-chain olefin to obtain a compound derived from the above second straight-chain olefin.

In a method for producing a compound according to an aspect of the present invention, the above second step may be a step of obtaining a compound derived from the above second straight-chain olefin and a composition containing the above first straight-chain olefin, and the above composition obtained in the second step may be reused as a portion or all of the above first raw material compound.

In a method for producing a compound according to an aspect of the present invention, the above second step may be a step of contacting the above second raw material compound with a dehydrogenation catalyst to obtain a conjugated diene by the dehydrogenation reaction of the above second straight-chain olefin.

In a method for producing a compound according to an aspect of the present invention, the above second step may be a step of contacting the above second raw material compound with a hydroformylation catalyst to obtain an aldehyde by the hydroformylation reaction of the above second straight-chain olefin.

A method for producing a compound according to an aspect of the present invention may comprise a step of contacting a raw material compound containing a first straight-chain olefin with a group of catalysts containing the above isomerization catalyst in the presence of 20 ppm by volume or more of molecular oxygen and/or water to obtain a compound derived from an isomerized product of the above first straight-chain olefin.

In a method for producing a compound according to an aspect of the present invention, the above group of catalysts may further comprise a dehydrogenation catalyst, and a compound derived from an isomerized product of the above first straight-chain olefin may be a conjugated diene.

In a method for producing a compound according to an aspect of the present invention, the above group of catalysts may further comprise a hydroformylation catalyst, and a compound derived from an isomerized product of the above first straight-chain olefin may be a aldehyde.

In a method for producing a compound according to an aspect of the present invention, the above step may be a step of obtaining a compound derived from an isomerized product of the above first straight-chain olefin and an unreacted material containing the above first straight-chain olefin, and the above unreacted material obtained in the above step may be reused as a portion or all of the above raw material compound.

Advantageous Effects of Invention

According to the present invention, an isomerization catalyst enabling the efficient isomerization reaction of an olefin with catalyst deterioration suppressed enough under even conditions where oxygen or water exists substantially is provided. According to the present invention, a method for producing a straight-chain olefin, enabling the efficient production of a target olefin with catalyst deterioration suppressed enough under even conditions where oxygen or water exists substantially is also provided. Additionally, according to the present invention, a method for producing a compound, enabling obtaining a compound derived from a straight-chain olefin efficiently is provided.

DESCRIPTION OF EMBODIMENTS

Preferred embodiments of the present invention will be described hereinafter. However, the present invention is not limited to the following embodiments at all.

A method for producing a straight-chain olefin according to the present embodiment comprises a step of contacting a raw material compound containing a first straight-chain olefin with an isomerization catalyst in the presence of 20 ppm by volume or more of molecular oxygen and/or water (steam) to isomerize at least a portion of the first straight-chain olefin to a second straight-chain olefin different therefrom in double bond position.

In this embodiment, an isomerization catalyst contains Si and Al. The isomerization reaction of an olefin can be performed efficiently with catalyst deterioration suppressed enough by using such an isomerization catalyst even when 20 ppm by volume or more of molecular oxygen (hereinafter also just called oxygen) and/or 20 ppm by volume or more of water exists in a system of reaction.

As to the isomerization of a straight-chain olefin, for example, the isomerization of 2-butene to 1-butene is limited by the thermodynamical equilibrium of n-butene isomers, and is promoted by high temperatures. A maximum concentration that 1-butene in n-butene can reach is known to be around 22% at 400° C. and around 30% at 500° C. by a thermodynamical equilibrium when n-butene passes through a reactor once (for example, Japanese Unexamined Patent Publication No. H8-224470). In a method for producing a straight-chain olefin according to this embodiment, isomerization can be attained to an almost maximum degree thermodynamically possible even in the presence of oxygen and/or water, and the catalytic activity is maintained over a long period of time.

In a method for producing a straight-chain olefin according to this embodiment, isomerization is performed in the presence of oxygen and/or water. In an isomerization reaction in which conventional isomerization catalysts are used, isomerization is usually performed in conditions where oxygen and water do not exist (especially oxygen does not exist), many side reactions such as complete oxidation reactions occur when oxygen exists, and it is difficult to advance the isomerization of an olefin selectively. Meanwhile, in a method for producing a straight-chain olefin according to this embodiment, the isomerization reaction of an olefin can be efficiently advanced since side reactions are suppressed enough, and an isomerization reaction can be performed over a long period of time since the durability of a catalyst is excellent.

In a method for producing a straight-chain olefin according to this embodiment, for example, a raw material compound can be supplied from a reaction of the preceding stage without removing oxygen and water since the isomerization reaction of an olefin proceeds efficiently as described above even in the presence of oxygen and/or water, and this is very advantageous for a process.

A method for producing a straight-chain olefin according to this embodiment can be performed at the same time as other reactions in which the isomerized second straight-chain olefin is consumed. Here, since an isomerization catalyst according to this embodiment can advance the isomerization reaction of an olefin efficiently even in the presence of oxygen and/or water, a reaction that proceeds in the presence of oxygen or water can be selected as the other reactions. For example, the oxidative dehydrogenation reaction of an olefin and the hydroformylation reaction of an olefin can be selected as the other reactions.

In this embodiment, an isomerization catalyst and a catalyst (for example, a dehydrogenation catalyst or a hydroformylation catalyst) of the other reaction may be mixed, and an isomerization reaction and another reaction may be performed simultaneously. In this case, since a second straight-chain olefin is generated by isomerization reaction according to a thermodynamical equilibrium while the second straight-chain olefin is consumed by other reactions, the apparent isomerization reaction reactivity can be improved.

In this embodiment, a first straight-chain olefin may be a straight-chain monoolefin. The number of carbon atoms of the first straight-chain monoolefin may be 4 to 8, and may be 4.

A first straight-chain olefin may be an internal olefin and may be a terminal olefin.

A first straight-chain olefin may be a straight-chain olefin selected from the group consisting of, for example, 1-butene, trans-2-butene, cis-2-butene, 1-pentene, 2-pentene, 1-hexene, 2-hexene, 3-hexene, 1-octene, 2-octene, 3-octene, and 4-octene. As the first straight-chain olefin, one of such straight-chain olefins may be used alone, and two or more of such straight-chain olefins may be used in combination.

A first straight-chain olefin may have a substituent containing a heteroatom such as oxygen, nitrogen, halogens, or sulfur. Such a substituent may be at least one selected from the group consisting of halogen atoms (—F, —Cl, —Br and —I), a hydroxyl group (—OH), an alkoxy group (—OR), a carboxyl group (—COOH), an ester group (—COOR), an aldehyde group (—CHO), and an acyl group (—C(=O)R). The raw material containing the straight-chain olefin having a substituent may be, for example, alcohols, may be ethers, and may be biofuels.

An isolated straight-chain olefin itself does not need to be used as a first straight-chain olefin, which can be used in the form of any mixture if needed. When a first straight-chain olefin is butene, for example, a raw material compound may be a fraction that is obtained by the fluid catalytic cracking of a heavy oil fraction and the number of carbon atoms of which is 4, and may be a fraction that is obtained by the pyrolysis of naphtha and the number of carbon atoms of which is 4.

In this embodiment, a raw material compound may contain other components beside a first straight-chain olefin. Other components may be, for example, an isomerized product of a first straight-chain olefin (a second straight-chain olefin may be contained), a saturated hydrocarbon compound or a diene. The saturated hydrocarbon compound and the diene may have, for example, the same number of carbon atoms as a first straight-chain olefin. The saturated hydrocarbon compound may be, for example, n-butane or cyclobutane. The diene may be, for example, butadiene. The raw material compound containing a first straight-chain olefin may contain impurities such as hydrogen, nitrogen, carbon monoxide, carbon dioxide gas, and methane as long as the effect of the present invention is not inhibited. As the raw material compound, a raw material compound consisting of only a straight-chain monoolefin may be used.

In this embodiment, although the concentration of a first straight-chain olefin in the raw material compound is not limited in particular, the economical efficiency tends to increase as the concentration of the straight-chain monoolefin in the raw material compound become higher.

A second straight-chain olefin is an isomer different in a double bond position from a first straight-chain olefin. Examples of the second straight-chain olefin include compounds exemplified as a first straight-chain olefin. A second straight-chain olefin may be an internal olefin, and may be a terminal olefin.

In a preferred aspect, a first straight-chain olefin may be an internal olefin, and a second straight-chain olefin may be a terminal olefin. A first straight-chain olefin may be 2-butene, and a second straight-chain olefin may be 1-butene.

Isomerization catalysts in this embodiment will be described in detail hereinafter.

An isomerization catalyst is a solid catalyst that catalyzes the isomerization reaction of a straight-chain olefin (the positional isomerization of an olefin), and contains Si and Al.

The isomerization catalyst may contain an inorganic oxide and may contain Si and Al as inorganic oxides. Namely, the isomerization catalyst may contain silica and alumina. Here, "contain silica and alumina" means containing Si and Al as inorganic oxides, and a composite oxide (for example, silica-alumina and zeolite) is also included.

The isomerization catalyst may contain one or two or more inorganic oxides selected from the group consisting of silica-alumina and zeolite, and may consist of the inorganic oxide.

Crystalline aluminosilicate named zeolite generically has fine spaces (nano-spaces) of the molecular size in one crystal. Zeolites are classified according to their crystal structures, and there are many types of zeolites such as LTA (A type), MFI (ZSM-5 type), MOR, BEA, FER, FAU (X type, Y type), SAPO, and ALPO. The isomerization catalyst may contain any one zeolite among these, and may contain two or more zeolites.

In the isomerization catalyst, the molar ratio (Si/Al) of Si to Al may be 5.0 or more, may be 100 or more, and may be 200 or more. The above molar ratio (Si/Al) may be 10000 or less, may be 3000 or less, and may be 2000 or less. The catalyst deterioration of an isomerization catalyst having such a ratio in the presence of oxygen and/or water tends to be suppressed more notably.

The isomerization catalyst may be a catalyst in which a metallic element is supported on the above inorganic oxide. A supported metallic element (hereinafter also called a support metallic element) may not be limited in particular, and may be, for example, an alkali metal, an alkaline earth metal or a transition metal.

A method for supporting a support metallic element is not limited in particular, for example, may be an impregnation method, a precipitator method, a coprecipitation method, a kneading method, an ion exchange method or a pore-filling method.

The supply sources of support metallic elements may be at least one selected from the group consisting of, for example, oxides, nitrates, carbonates, ammonium salts, hydroxides, carboxylates, ammonium carboxylates, ammonium halides, hydroacids (for example, chloroplatinic acid ($H_2PtCl_6$)), acetylacetonates, and alkoxides.

The content of a support metallic element in an isomerization catalyst is not limited in particular, and may be, for example, 0.01 to 100 parts by mass and may be 0.1 to 50 parts by mass on the basis of 100 parts by mass of an inorganic oxide. The content of a support metallic element can be determined by inductively coupled plasma atomic emission spectrophotometry (ICP emission spectrophotometry).

Ammonia temperature programmed desorption (ammonia TPD or $NH_3$-TPD) is known widely as an effective method for characterizing the acidity of catalysts. For example, C. V. Hidalgo et al., Journal of Catalysis, vol. 85, pp. 362-369 (1984) discloses that the amount of Broensted acid sites or the distribution of the acid strength of Broensted acid sites can be measured by ammonia TPD.

The ammonia TPD involves allowing ammonia, which is a base probe molecule, to be adsorbed onto a sample solid and measuring simultaneously the amount and the temperature of ammonia desorbed by continuously increasing the temperature. Ammonia adsorbed to weak acid sites would desorb at low temperatures (corresponding to desorption from sites where heat of adsorption is in a low range) and ammonia adsorbed to strong acid sites would desorb at high temperatures (corresponding to desorption from sites where heat of adsorption is in a high range). In such ammonia TPD, the acid strength is indicated by the temperature or the amount of heat of adsorption without a color reaction and therefore more accurate values of the solid acid strength and the solid acid amount will be obtained, which makes appropriate characterization of isomerization catalysts possible.

The amount of the acid sites (acidity amount) of an isomerization catalyst can be determined by ammonia TPD in which the ammonia adsorption amount is measured under measurement conditions described in "Niwa, Zeolite, 10, 175 (1993)" by a device described therein.

The amount $A_1$ of the total acid sites of an isomerization catalyst (the total acidity amount) may be 0.11 mmol/g or less, may be 0.09 mmol/g or less, may be 0.03 mmol/g or less, may be 0.015 mmol/g or less, and may be 0.010 mmol/g or less. When the total acidity amount is in the above ranges, side reactions such as skeletal isomerization and $CO_2$ generation, the catalyst deterioration by coke precipitation and the like tend to be suppressed. The total acidity amount $A_1$ of an isomerization catalyst may be 0.001 mmol/g or more, and may be 0.003 mmol/g or more.

In an isomerization catalyst, the ratio $A_2/A_1$ of the amount $A_2$ of acid sites measured in the temperature range of 600° C. or more to the total acidity amount $A_1$ may be 0.03 or more, may be 0.05 or more, may be 0.08 or more, may be 0.1 or more, and may be 0.15 or more. When the ratio $A_2/A_1$ is in the above ranges, side reactions such as skeletal isomerization and $CO_2$ generation and the catalyst deterioration by coke precipitation tend to be suppressed. The ratios $A_2/A_1$ may be 1.0 or less, and may be 0.7 or less.

An isomerization catalyst may be fired if needed. Firing may be performed in one stage, and may be performed in multistage of two or more stages. The firing temperature is not limited in particular. When firing is performed in one stage, the firing temperature may be, for example, 200 to 600° C. The firing time may be 1 to 10 hours. Firing may usually be performed on the circulation of air, and the atmosphere is not limited in particular at the time of firing.

As long as the physical properties of a catalyst and the performance of a catalyst are not deteriorated, an isomerization catalyst may contain a forming aid in view of improving ease of forming. A forming aid may be at least one selected from the group consisting of, for example, a thickener, a surfactant, a humectant, a plasticizer, and a binder raw material.

An isomerization catalyst may be formed by methods such as an extrusion method and a tablet compression method. A forming step may be performed in a suitable stage of a process for producing an isomerization catalyst in view of the reactivity of a forming aid and the like.

The shape of an isomerization catalyst is not limited in particular and can be suitably selected depending on the form in which a catalyst is used. For example, the shape of an isomerization catalyst may be a shape such as a pellet form, a granular form, a honeycomb form, and a sponge form.

Next, isomerization reactions and other reactions in this embodiment will be described in detail.

In this embodiment, the isomerization reaction of a first straight-chain olefin is performed by contacting a raw material compound containing a first straight-chain olefin with an isomerization catalyst in the presence of 20 ppm by volume or more of oxygen and/or water (steam). By this isomerization reaction, at least a portion of a first straight-chain olefin is isomerized to a second straight-chain olefin.

The amount of oxygen in a system of reaction may be 20 ppm by volume or more, may be 0.01% by volume or more, may be 0.1% by volume or more, and may be 0.5% by volume or more. The amount of oxygen may be 50% by volume or less, may be 30% by volume or less, and may be 20% by volume or less.

The amount of water in a system of reaction may be 20 ppm by volume or more, may be 0.01% by volume or more, may be 0.1% by volume or more, and may be 0.5% by volume or more. The amount of water may be 50% by volume or less, may be 30% by volume or less, and may be 20% by volume or less.

An isomerization reaction may be performed under conditions where other components beside a raw material compound, oxygen, and water further exist as long as the effect of the present invention is not inhibited. Here, the other components may be methane, hydrogen, nitrogen, carbon dioxide, carbon monoxide, and the like.

An isomerization reaction may be a gas-solid catalytic reaction and may be a liquid-solid catalytic reaction. A gas-solid catalytic reaction indicates a reaction performed by contacting a gas phase raw material with a solid phase isomerization catalyst, and a liquid-solid catalytic reaction indicates a reaction performed by contacting a liquid phase raw material with a solid phase isomerization catalyst.

An isomerization reaction may be performed by passing a raw material, for example, through a reactor into which an isomerization catalyst is filled.

In an isomerization reaction, oxygen and water existing in a system of reaction may be supplied to a reactor together with a raw material compound. Namely, an isomerization reaction may be performed by passing a raw material gas containing a raw material compound containing a first straight-chain olefin, and 20 ppm by volume or more of oxygen and/or water through a reactor filled with an isomerization catalyst.

The amount of oxygen in a raw material gas may be 20 ppm by volume or more, may be 0.01% by volume or more, may be 0.1% by volume or more, and may be 0.5% by volume or more. The amount of oxygen in a raw material gas may be 50% by volume or less, may be 30% by volume or less, and may be 20% by volume or less.

The amount of water in a raw material gas may be 20 ppm by volume or more, may be 0.01% by volume or more, may be 0.1% by volume or more, and may be 0.5% by volume or more. The amount of water in a raw material gas may be 50% by volume or less, may be 30% by volume or less, and may be 20% by volume or less.

As long as a raw material gas does not inhibit the effect of the invention, a raw material gas may contain any impurities. Such an impurity may be, for example, nitrogen, argon, neon, helium, carbon monoxide, or carbon dioxide.

In this embodiment, a compound derived from a second straight-chain olefin may be produced by submitting the second straight-chain olefin generated by an isomerization reaction to other reactions.

Namely, a method for producing a compound according to the embodiment may comprise: a first step of contacting a first raw material compound containing a first straight-chain olefin with an isomerization catalyst in the presence of 20 ppm by volume or more of molecular oxygen and/or water to isomerize at least one portion of the first straight-chain olefin to a second straight-chain olefin different therefrom in double bond position; and a second step of reacting a second raw material compound containing the second straight-chain olefin to obtain a compound derived from the second straight-chain olefin.

The first step may be performed according to a preferred aspect of the above isomerization reaction. Various reactions in which the second straight-chain olefin is reacted can be applied to the second step, and well-known reaction conditions may be applied to the reaction condition thereof.

The second step may be performed, for example, by passing a raw material gas containing the second raw material compound through a reactor filled with a reaction catalyst.

A produced gas isomerized in the first step may be used as the second raw material compound in the second step. For example, the first step may be a step of passing a raw material gas containing the first raw material compound through the first reactor filled with an isomerization catalyst to obtain a produced gas containing the second straight-chain olefin, and the second step may be a step of passing the produced gas obtained in the first step through the second reactor filled with a reaction catalyst and reacting the second straight-chain olefin.

The second step may be a step of obtaining a target compound derived from the second straight-chain olefin and a composition containing the first straight-chain olefin. Here, the first straight-chain olefin in the composition may be, for example, the first straight-chain olefin contained in the second raw material compound submitted to the second step (for example, the produced gas in the first step), and may be the first straight-chain olefin generated in a reaction of the second step.

When the composition containing the first straight-chain olefin is obtained at the second step, the composition may be reused as a portion or all of the first raw material compound in the first step. Since the isomerization reaction of an olefin proceeds efficiently even in the presence of oxygen and water in the first step, oxygen and water do not need to be removed at the time of such a reuse, and the efficiency of the whole process is excellent.

The second step may be a step of generating a conjugated diene by the oxidative dehydrogenation reaction of the second straight-chain olefin. At this time, the second step may be a step of contacting the second raw material compound with a dehydrogenation catalyst to obtain a conjugated diene.

Reaction conditions of oxidative dehydrogenation reactions are not limited in particular, and various well-known reaction conditions may be applied. For example, reaction conditions may be 400° C. and 0.1 MPaG.

A well-known catalyst for a dehydrogenation reaction can be used as a dehydrogenation catalyst. Examples of the dehydrogenation catalyst include a multicomponent molybdenum-bismuth-based catalyst, a ferrite catalyst, a vanadium-magnesium-based catalyst, and a cobalt-molybdenum-based catalyst.

The second step may be a step of generating an aldehyde by the hydroformylation reaction of the second straight-chain olefin. At this time, the second step may be a step of contacting the second raw material compound with a hydroformylation catalyst to obtain an aldehyde.

Reaction conditions of a hydroformylation reaction are not limited in particular, and various well-known reaction conditions may be applied. For example, reaction conditions may be 150° C. and 1.5 MPa.

A well-known catalyst for a hydroformylation reaction can be used as a hydroformylation catalyst. Examples of the hydroformylation catalyst include a rhodium catalyst and a cobalt catalyst.

In this embodiment, another reaction consuming the isomerized second straight-chain olefin may be performed simultaneously with an isomerization reaction.

Since the isomerization catalyst can advance the isomerization reaction of an olefin efficiently even in the presence of oxygen and/or water, a reaction that proceeds in the presence of oxygen or water can be selected as the above other reaction. For example, the oxidative dehydrogenation reaction of an olefin and the hydroformylation reaction of an olefin or the like can be selected as the above other reaction.

According to this embodiment, an isomerization catalyst and a catalyst of the above other reaction (for example, a dehydrogenation catalyst or a hydroformylation catalyst) may be mixed, and an isomerization reaction and the above other reaction may be performed simultaneously. In this case, since the second straight-chain olefin is generated by an isomerization reaction according to a thermodynamical equilibrium while the second straight-chain olefin is consumed by another reaction, the apparent reactivity of an isomerization reaction can be improved.

Namely, a method for producing a compound of this compound containing the first straight-chain olefin with a group of catalysts containing an isomerization catalyst in the presence of 20 ppm by volume or more of molecular oxygen and/or water to obtain a compound derived from an isomerized product of the first straight-chain olefin. Here, the isomerized product of the first straight-chain olefin may be the above second straight-chain olefin.

According to an intended reaction, the group of catalyst contains a catalyst beside an isomerization catalyst. For example, the above other reaction may be an oxidative dehydrogenation reaction, and the group of catalysts may contain an isomerization catalyst and a dehydrogenation catalyst at this time. The above other reaction may be a hydroformylation reaction, and the group of catalysts may contain an isomerization catalyst and a hydroformylation catalyst at this time. The same catalyst as described above can be exemplified as a dehydrogenation catalyst and a hydroformylation catalyst.

In this aspect, the above step may be performed by passing a raw material gas containing the raw material compound through a reactor filled with the group of catalysts.

The above step may be a step of obtaining a target compound derived from the isomerized product of the first straight-chain olefin and an unreacted material containing the first straight-chain olefin. At this time, the unreacted material may be reused as a portion or all of the raw material compound in the above step. Since the isomerization reaction of an olefin proceeds efficiently even in the presence of oxygen and water in the above step, oxygen and water do not need to be removed at the time of such a reuse, and the efficiency of the whole process is excellent.

Although preferred embodiments of the present invention were described above, the present invention is not limited to the above embodiments.

EXAMPLES

Although the present invention will be described more specifically by illustrating Examples hereinafter, the present invention is not limited to these Examples.

Example 1

A tube type reactor (tube made of SUS) was filled with 0.3 cc of an H-β zeolite catalyst (produced by Tosoh Corporation, Si/Al=250 (mol/mol)). The inner diameter of the tube type reactor was 14 mm, and the total length thereof was 60 cm. The top and bottom of the catalyst was filled with glass beads. The mean particle diameter of the glass beads was 1 mm. After connecting this reactor to a flow reaction device, the temperature in the reactor was raised to 350° C. by using an electric furnace. A raw material containing olefins (raw material gas), a mixed gas of oxygen and nitrogen (the oxygen concentration is 10%), and water (steam) were supplied to the reactor in which the temperature was raised. The isomerization reaction of an olefin was performed in the above procedure.

The inlet velocities of a raw material gas, air and water (steam) to the reactor were as follows, respectively. The oxygen concentration in the gas supplied to the reactor was 8.5% by volume, and the water concentration was 7.1% by volume. The composition of the raw material gas is shown in Table 1.

The inlet velocity of the raw material gas: 3.3 g/h.

The inlet velocity of a mixed gas of oxygen and nitrogen (the oxygen concentration was 10%): 222 cc/min.

The inlet velocity of water (steam): 0.9 g/h

TABLE 1

| Raw Material Gas Composition | (% by Mass) |
| --- | --- |
| cis-2-Butene | 28.9 |
| trans-2-Butene | 43.5 |
| 1-Butene | 0.0 |
| Isobutene | 0.2 |
| Normal butane | 27.4 |

When 60 minutes and 240 minutes passed from a reaction start time, the product of isomerization reaction (produced gas) was sampled. The time when the raw material gas started to be supplied was defined as a reaction start time (0 minutes). The sampled produced gas was analyzed by using a gas chromatograph provided with a hydrogen flame ionization detector and a gas chromatograph provided with a thermal conductivity detector. The concentrations of components in produced gases were quantified by the absolute calibration method.

Example 2

The isomerization reaction of an olefin was performed similarly to Example 1 except that a zeolite catalyst of H-ZSM-5 (produced by Tosoh Corporation, Si/Al=940 (mol/mol)) was used as an isomerization catalyst.

Example 3

The isomerization reaction of an olefin was performed similarly to Example 1 except that a zeolite catalyst of SAPO-34 produced with reference to Comparative Example 2 of Japanese Unexamined Patent Publication No. 2012-91997 was used as an isomerization catalyst.

Example 4

The isomerization reaction of an olefin was performed similarly to Example 1 except that a zeolite catalyst of H-USY (produced by Tosoh Corporation, Si/Al=5 (mol/mol)) was used as an isomerization catalyst.

Example 5

The isomerization reaction of an olefin was performed similarly to Example 1 except that a zeolite catalyst of H-β (produced by Tosoh Corporation, Si/Al=14.5 (mol/mol)) was used as an isomerization catalyst.

Example 6

The isomerization reaction of an olefin was performed similarly to Example 1 except that a silica alumina catalyst (IS-28N produced by JGC Catalysts and Chemicals Ltd.) was used as an isomerization catalyst.

Example 7

The isomerization reaction of an olefin was performed similarly to Example 1 except that a silica-alumina catalyst (F-24X produced by N.E. CHEMCAT Corporation) was used as an isomerization catalyst.

Comparative Example 1

The isomerization reaction of an olefin was performed similarly to Example 1 except that a silica-titania catalyst produced with reference to Example (Catalyst C) of Japanese Unexamined Patent Publication No. 2012-566 was used as an isomerization catalyst.

Comparative Example 2

The isomerization reaction of an olefin was performed similarly to Example 1 except that a MCM-41 catalyst (mesoporous silica produced by Sigma-Aldrich Co. LLC.) was used as an isomerization catalyst. The composition of produced gases at 60 minutes after and 240 minutes after was as shown in Table 3.

Comparative Example 3

The isomerization reaction of an olefin was performed similarly to Example 1 except that a silica-calcia catalyst produced with reference to Example 1 of Japanese Unexamined Patent Publication No. H9-103675 was used as an isomerization catalyst.

Comparative Example 4

To 1 L of ion exchanged water were added 105.5 g of $Al(NO_3)_3.9H_2O$ and 54.1 g of $Mg(NO_3)_2.6H_2O$, and the mixture was stirred vigorously. A two times dilution of concentrated ammonia water was dropped at a rate of 0.1 mL/s with the aqueous solution stirred until the pH was adjusted to 10, and the mixture was then stirred for 30 minutes and thereafter left to stand for 30 minutes. The precipitate was filtered and washed with ion exchanged water twice. The obtained precipitate was dried at 130° C. for 12 hours and thereafter fired under air circulation in three stages: at 300° C. for one hour, at 500° C. for two hours and at 800° C. for four hours to obtain a magnesia-alumina catalyst.

The isomerization reaction of an olefin was performed similarly to Example 1 except that this magnesia-alumina catalyst was used as an isomerization catalyst.

Comparative Example 5

With reference to Japanese Unexamined Patent Publication No. S62-197147, γ alumina (NKHD-24 produced by Sumitomo Chemical Company, Limited) is immersed in an aqueous solution prepared by mixing magnesium nitrate hexahydrate and water at a weight ratio of 80:20, thereafter dried at 110° C. for 12 hours and fired at 500° C. for three hours five times repeatedly to obtain a magnesium oxide catalyst (Mg: 23% by mass).

The isomerization reaction of an olefin was performed similarly to Example 1 except that this magnesium oxide catalyst was used as an isomerization catalyst.

When the Si/Al ratio (molar ratio) was measured and the total acidity amount $A_1$ and the acidity amount $A_2$ measured at 600° C. or more were measured by ammonia TPD as to isomerization catalysts of Examples 1 to 7, and results were as shown in Table 2. The composition of produced gases at 60 minutes after and 240 minutes after in Examples 1 to 7 was as shown in Table 3 and 4, respectively. The ratio $C_{1h}/C_{4h}$ of the amount $C_{1h}$ of 1-butene in a produced gas at 60 minutes after (one hour after) to the amount $C_{4h}$ of 1-butene of the produced gas at 240 minutes after (four hours after) was described as the catalyst deterioration degree in Table 4.

The composition of produced gases at 60 minutes after in Comparative Examples 1 to 5 was as shown in Table 5, respectively.

TABLE 2

|  | Example 1 | Example 2 | Example 3 | Example 4 |
|---|---|---|---|---|
| Si/Al Ratio | 250 | 940 | 0.1 | 5 |
| Total Acidity Amount $A_1$ (mmol/g) | 0.00343 | 0.00520 | 0.10587 | 0.12199 |
| Acidity Amount at 600° C. or more $A_2$ (mmol/g) | 0.00108 | 0.00024 | 0.00647 | 0.01339 |
| Ratio $A_2/A_1$ | 0.313 | 0.047 | 0.061 | 0.11 |

|  | Example 5 | Example 6 | Example 7 |
|---|---|---|---|
| Si/Al Ratio | 14.5 | 4.1 | 8 |
| Total Acidity Amount $A_1$ (mmol/g) | 0.08846 | 0.02144 | 0.01541 |
| Acidity Amount at 600° C. or more $A_2$ (mmol/g) | 0.00978 | 0.00191 | 0.00412 |
| Ratio $A_2/A_1$ | 0.111 | 0.089 | 0.268 |

TABLE 3

|  |  | Example 1 | Example 2 | Example 3 | Example 4 |
|---|---|---|---|---|---|
| Product Composition (After 1 h) (% by Mass) | cis-2-Butene | 24.3 | 23.7 | 23.9 | 24.8 |
|  | trans-2-Butene | 35.6 | 36.4 | 37.4 | 38.8 |
|  | 1-Butene | 13.0 | 12.4 | 11.0 | 8.7 |
|  | Isobutene | 0.2 | 0.2 | 0.2 | 0.2 |
|  | Normal butane | 26.9 | 27.0 | 27.4 | 27.4 |
|  | C1 to C3 Hydrocarbon | 0.0 | 0.2 | 0.0 | 0.0 |
|  | $CO_2$ | 0.0 | 0.1 | 0.1 | 0.1 |
|  | Butadiene | 0.0 | 0.0 | 0.0 | 0.0 |
| Product Composition (After 4 h) (% by Mass) | cis-2-Butene | 24.2 | 23.9 | 24.3 | 26.2 |
|  | trans-2-Butene | 35.3 | 37.1 | 38.4 | 40.8 |
|  | 1-Butene | 13.5 | 11.8 | 9.6 | 5.4 |
|  | Isobutene | 0.2 | 0.2 | 0.2 | 0.2 |
|  | Normal butane | 26.9 | 26.9 | 27.4 | 27.3 |
|  | C1 to C3 Hydrocarbon | 0.0 | 0.0 | 0.0 | 0.0 |
|  | $CO_2$ | 0.0 | 0.1 | 0.1 | 0.1 |
|  | Butadiene | 0.0 | 0.0 | 0.0 | 0.0 |
| Catalyst Deterioration Degree (Ratio $C_1/C_4$) |  | 1.04 | 0.95 | 0.87 | 0.63 |

TABLE 4

|  |  | Example 5 | Example 6 | Example 7 |
|---|---|---|---|---|
| Product Composition (After 1 h) (% by Mass) | cis-2-Butene | 25.4 | 23.3 | 24.7 |
|  | trans-2-Butene | 38.7 | 35.0 | 38.4 |
|  | 1-Butene | 8.9 | 14.2 | 9.0 |
|  | Isobutene | 0.2 | 0.3 | 0.2 |
|  | Normal butane | 26.7 | 27.1 | 27.4 |
|  | C1 to C3 Hydrocarbon | 0.0 | 0.0 | 0.0 |
|  | $CO_2$ | 0.1 | 0.1 | 0.1 |
|  | Butadiene | 0.0 | 0.0 | 0.1 |
| Product Composition (After 4 h) (% by Mass) | cis-2-Butene | 26.3 | 23.9 | 25.4 |
|  | trans-2-Butene | 40.8 | 37.1 | 39.7 |
|  | 1-Butene | 6.2 | 11.7 | 7.0 |
|  | Isobutene | 0.2 | 0.2 | 0.2 |
|  | Normal butane | 27.5 | 26.9 | 27.4 |
|  | C1 to C3 Hydrocarbon | 0.0 | 0.0 | 0.0 |
|  | $CO_2$ | 0.1 | 0.1 | 0.1 |
|  | Butadiene | 0.0 | 0.0 | 0.2 |
| Catalyst Deterioration Degree (Ratio $C_1/C_4$) |  | 0.69 | 0.83 | 0.77 |

TABLE 5

|  |  | Comparative Example 1 | Comparative Example 2 | Comparative Example 3 | Comparative Example 4 | Comparative Example 5 |
|---|---|---|---|---|---|---|
| Product Composition (After 1 h) (% by Mass) | cis-2-Butene | 26.4 | 26.4 | 28.4 | 28.5 | 29.8 |
|  | trans-2-Butene | 41.3 | 41.6 | 43.7 | 43.6 | 41.8 |
|  | 1-Butene | 4.2 | 4.4 | 0.3 | 0.3 | 0.6 |
|  | Isobutene | 0.2 | 0.2 | 0.2 | 0.2 | 0.2 |
|  | Normal butane | 27.5 | 27.4 | 27.4 | 27.3 | 27.7 |
|  | C1 to C3 Hydrocarbon | 0.0 | 0.0 | 0.0 | 0.0 | 0.0 |
|  | $CO_2$ | 0.1 | 0.0 | 0.0 | 0.1 | 0.0 |
|  | Butadiene | 0.2 | 0.0 | 0.0 | 0.0 | 0.0 |

The invention claimed is:

1. An isomerization catalyst adapted to isomerize a first straight-chain olefin to a second straight-chain olefin different therefrom in a double bond position in the presence of 20 ppm by volume or more of molecular oxygen, comprising:
   Si; and
   Al;
   wherein an amount $A_1$ of total acid sites measured by ammonia temperature programmed desorption is 0.11 mmol/g or less
   wherein a ratio $A_2/A_1$ of an amount $A_2$ of acid sites measured in a temperature range of 600° C. or more to the amount $A_1$ of the total acid sites measured by ammonia temperature programmed desorption is 0.03 or more.

2. The isomerization catalyst according to claim 1, wherein a ratio $A_2/A_1$ of an amount $A_2$ of acid sites measured in a temperature range of 600° C. or more to the amount $A_1$ of the total acid sites measured by ammonia temperature programmed desorption is 0.03 or more.

3. The isomerization catalyst according to claim 1, comprising a zeolite.

4. The isomerization catalyst according to claim 1, wherein a molar ratio of Si to Al (Si/Al) is 100 or more.

5. A method for producing a straight-chain olefin, comprising:
   a step of contacting a raw material compound comprising a first straight-chain olefin with the isomerization catalyst according to claim 1 in the presence of 20 ppm by volume or more of molecular oxygen to isomerize at least a portion of the first straight-chain olefin to the second straight-chain olefin different therefrom in double bond position.

6. The production method according to claim 5, wherein the numbers of carbon atoms of the first straight-chain olefin and the second straight-chain olefin are 4 to 8.

7. The production method according to claim 5, wherein the step is performed under conditions for a gas-solid catalytic reaction.

8. A method for producing a compound comprising:
   a first step of contacting a first raw material compound comprising a first straight-chain olefin with the isomerization catalyst according to claim 1 in the presence of 20 ppm by volume or more of molecular oxygen to isomerize at least a portion of the first straight-chain olefin to a second straight-chain olefin different therefrom in double bond position; and
   a second step of reacting a second raw material compound comprising the second straight-chain olefin to obtain a compound derived from the second straight-chain olefin.

9. The production method according to claim 8, wherein the second step is a step of obtaining the compound derived from the second straight-chain olefin and a composition comprising the first straight-chain olefin, and
   the composition obtained in the second step is reused as a portion or all of the first raw material compound.

10. The production method according to claim 8, wherein the second step is a step of contacting the second raw material compound with a dehydrogenation catalyst to obtain a conjugated diene by the dehydrogenation reaction of the second straight-chain olefin.

11. The production method according to claim 8, wherein the second step is a step of contacting the second raw material compound with a hydroformylation catalyst to obtain an aldehyde by the hydroformylation reaction of the second straight-chain olefin.

12. A method for producing a compound, comprising:
   a step of contacting a raw material compound comprising a first straight-chain olefin with a group of catalysts comprising the isomerization catalyst according to claim 1 in the presence of 20 ppm by volume or more of molecular oxygen to obtain a compound derived from an isomerized product of the first straight-chain olefin.

13. The production method according to claim 12, wherein the group of catalysts further comprises a dehydrogenation catalyst, and
   the compound derived from the isomerized product of the first straight-chain olefin is a conjugated diene.

14. The production method according to claim 12, wherein the group of catalysts further comprises a hydroformylation catalyst, and
   the compound derived from the isomerized product of the first straight-chain olefin is an aldehyde.

15. The production method according to claim 12, wherein the step is a step of obtaining the compound derived from the isomerized product of the first straight-chain olefin and an unreacted material comprising the first straight-chain olefin, and
   the unreacted material obtained in the step is reused as a portion or all of the raw material compound.

* * * * *